(12) United States Patent
Steinborn et al.

(10) Patent No.: US 6,518,025 B1
(45) Date of Patent: Feb. 11, 2003

(54) QUANTIFICATION BY INHIBITION OF AMPLICATION

(75) Inventors: Ralf Steinborn, Vienna (AT); Mathias Müller, Vienna (AT); Gottfried Brem, Hilgertshausen (DE); Dieter Klein, Tulln (AT)

(73) Assignee: Bavarian Nordic Research Institute A/S, Glostrup (DK)

( * ) Notice: Subject to any disclaimer, the term of this patent is extended or adjusted under 35 U.S.C. 154(b) by 0 days.

(21) Appl. No.: 09/632,171

(22) Filed: Aug. 3, 2000

Related U.S. Application Data

(63) Continuation of application No. PCT/EP99/00648, filed on Feb. 2, 1999.

(30) Foreign Application Priority Data

Feb. 5, 1998 (DK) .............................................. 0158/98

(51) Int. Cl.⁷ ........................... C12Q 1/68; C12P 19/34; C07H 21/02
(52) U.S. Cl. ....................... 435/6; 435/91.2; 536/24.31; 536/24.33
(58) Field of Search ................. 435/6, 91.2; 536/24.31, 536/24.33

(56) References Cited

U.S. PATENT DOCUMENTS

| | | | |
|---|---|---|---|
| 5,210,015 A | 5/1993 | Gelfand et al. ................. | 435/6 |
| 5,487,972 A | 1/1996 | Gelfand et al. ................. | 435/6 |
| 5,521,301 A | 5/1996 | Wallace et al. ........... | 536/24.33 |
| 5,639,611 A | 6/1997 | Wallace et al. ................. | 435/6 |
| 5,780,233 A | 7/1998 | Guo et al. ...................... | 435/6 |
| 5,804,375 A | 9/1998 | Gelfand et al. ................. | 435/6 |

FOREIGN PATENT DOCUMENTS

| | | |
|---|---|---|
| EP | 0 812 922 | * 12/1997 |
| EP | 0 812 922 A2 | 12/1997 |
| WO | WO 92/02638 | 2/1992 |
| WO | WO 96/40995 | 12/1996 |
| WO | WO 97/46711 | 12/1997 |
| WO | WO 97/46714 | * 12/1997 |

OTHER PUBLICATIONS

Heid et al. Real time quantitative PCR. Genome Res., vol. 6: 986–994, 1996.*
Heid, C.A., et al., "Real Time Quantitative PCR," *Genome Research*, 6(10): 986–994 (Oct. 1, 1996).
Woudenberg, T.M., et al., "Quantitative PCR by Real Time Detection," *Proceedings of the SPIE*, 2860:306–315 (Jan. 1, 1996).
Guo, et al., "Enhanced Discrimination of Single Nucleotide Polymorphisms by Artificial Mismatch Hybridization," *Nature Biotechnologies*, 15:331–335 (1997).
Saperstein D.A. and Nickerson, J.M. "Restriction Fragment Length Polymorphism Analysis Using PCR Coupled to Restriction Digests," *Biotechniques*, 10(4):488–489 (1991).
Anderson, S., et al., "Complete Sequence of Bovine Mitochondrial DNA Conserved Features of the Mammalian Mitochondrial Genome," *J. Mol. Biol.*, 156:683–717 (1982).
Johns, D.R., "The Other Human Genome: Mitochondrial DNA and Disease," *Nature Medicine*, 2:1065–1068 (1996).
Egensperger, R., et al., "Association of the Mitochondrial tRNA$^{A4336G}$ Mutation with Alzheimer's and Parkinson's Diseases," *Neuropathol. Appl. Neurobiol.*, 23(4):315–321 (1997).
Plante, Y., et al., "Restriction Fragment Length Polymorphism in the Mitochondrial DNA of Cloned Cattle," *Theriogenology*, 38:897–904 (1992).
Livak, K.J., et al., "Oligonucleotides with Fluorescent Dyes at Opposite Ends Provide a Quenched Probe System Useful for Detecting PCT Product and Nucleic Acid Hybridization," *PCR Methods Applic.*, 4:357–362 (1995).

* cited by examiner

*Primary Examiner*—Jeffrey Fredman
*Assistant Examiner*—Suryaprabha Chunduru
(74) *Attorney, Agent, or Firm*—Hamilton, Brook, Smith & Reynolds, P.C.

(57) ABSTRACT

The present invention provides a method of quantification of nucleic acid sequences with minimal alterations conducting a real time PCR quantification assay with allele-specific primers. Further, the present invention provides the method for quantifying allelic differences of bovine mitochondrial DNA sequences and allele-specific primers to be used in said method.

54 Claims, 1 Drawing Sheet

```
                            SEQUENCE LISTING

<160> NUMBER OF SEQ ID NOS:  14

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 1
accattgact gtaatgtcta t                                                  21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 2
gccccatgca tataagcagg t                                                  21

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 3
gcaagtacat gacctctaca c                                                  21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 4
ttgacggcca tagctgagtc c                                                  21

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence:primer

<400> SEQUENCE: 5
atgtatatag tacattaaat tacat                                              25

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 6
```
caccatcaac ccccaaagct                                          20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 7
cctgaagaaa gaaccagatg                                          20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 8
ttgggttaag ctacatcaac                                          20

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 9
cttaattacc atgccgcgtg a                                        21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 10
ccagctacaa tagatgctcc g                                        21

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence:primer

<400> SEQUENCE: 11
gtacttgctt atatgcatgg tgt                                      23

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence:primer

<400> SEQUENCE: 12
taattatatg tattatgtac ggg                                      23

<210> SEQ ID NO 13
<211> LENGTH: 18
<212> TYPE: DNA

```
<213> ORGANISM: Artificial Sequence
<220> FEATURE:
<223> OTHER INFORMATION: Description of Artificial Sequence:primer

<400> SEQUENCE: 13
ccagcataat gataacca                                              18

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence:primer

<400> SEQUENCE: 14
gagcaccagc ataatgataa acg                                        23
```

QUANTIFICATION BY INHIBITION OF AMPLICATION

RELATED APPLICATION(S)

This application is a continuation of PCT/EP99/00648, filed Feb. 2, 1999, which claims priority to DK 0158/98, filed Feb. 5, 1998. The entire teachings of PCT/EP99/00648 and DK 0158/98 are incorporated herein by reference.

BACKGROUND OF THE INVENTION

Screening for point mutations, small base pair deletions or insertions in genes causing diseases has lately gained growing interest especially considering the development of certain diseases among an ethnic group or the predisposition of an individual patient. A variety of mutation scanning techniques (Beaudet et al., 1995, The Metabolic and Molecular Bases of Inherited Disease, Vol. 1, McGraw-Hill, Inc., New York) with mutation detection rates up to and above 90% (Guo et al., *Nature Biotechnology*, 15: 331–335, (1997)) have been developed over the last decade.

However, even more of interest than the knowledge about the presence of a specific mutation in a nucleic acid sequence would be the knowledge about the amount of such mutated nucleic acid sequences.

The standard technique to quantify nucleic acid sequences with mutations is a notoriously laborious combination of a polymerase chain reaction (PCR), a labeled (e.g., radioactive) restriction enzyme digestion and phospho-imager quantification (Saperstein & Nickerson, *Biotechniques* 10(4): 488–489(1991)). Accordingly, the sequences to quantify are amplified in a PCR, the amplified products are incubated with restriction enzymes and radioactive labeled. Only the nucleic acid sequences that carry a specific mutation, thereby comprising an additional restriction enzyme recognition site, can be cleaved with the restriction enzyme. Such a restriction enzyme digest results in uncleaved amplification products, not comprising the mutation, and cleaved amplification products, because of the mutation. Depending on their size, these products are separated by gel electrophoresis separation. This gel or a membrane after southern blotting this gel is exposed to screen sensitive to radioactivity. Since all fragments are equally labeled by radioactivity, the stimulation, which correlates with the amount of amplification product and which is caused by the radioactive disintegration, can be detected. Thus, it is possible to quantify said stimulation and the amount of the different amplification products, respectively, with a phospho-imager.

Beside the time consuming setup, the limits of the detection range for quantification are reached if less than 5% of the allelic sequences of the genome carry a mutation. In other words, if only 1% or less of the nucleic acid sequences carries a mutation, this mutation is not detectable and, thus, cannot be quantified.

Additionally, not every mutation can be detected by this technique, because restriction enzymes that are able to distinguish between sequences with or without mutation are often not available.

Recently, considering the fact that PCR technology has been proven to be a powerful tool for nucleic acid analysis, a highly elaborate quantification assay for PCR products, the so called TaqMan™ PCR (PE Applied Biosystems, Germany), was suggested (Livak et al., *PCR Methods Applic.* 4:357–362(1995)).

The TaqMan™ technology is based on PCR wherein an additional specific, internal, fluorogenically labeled oligonucleotide probe is used. Typical amplicons range in size from 100 bp to 1200 bp. The probe specifically anneals between the forward (5') and reverse (3') PCR primer binding sites (the Figure). It consists of an oligonucleotide with a 5'-reporter dye (e.g., FAM, 6-carboxyfluorescein) and a quencher dye (e.g., TAMRA, 6-carboxytetramethylrhodamine) which compensates the emission spectra of the reporter dye as long as both dyes are attached to the probe. While performing the standard PCR, the 5'→3' exonuclease activity of conventional thermostable Taq polymerase is exploited, which degrades the internal fluorogenic probe thereby releasing the fluorogenic signal of the 5'-reporter dye. Thus, the fluorescence signals are detectable and can be quantified. An ABI PRISM™ Sequence Detection System (PE Applied Biosystems, Germany) is normally used to detect the fluorescent signals. An improvement of the TaqMan™ technology was the introduction of, instead of an endpoint measurement, the measurement of the released fluorescent emission continuously during the PCR amplification (Heid et al., *Genome Research*, 6:, 986–994 (1996)). Since the exponential accumulation of the fluorescent signal directly reflects the exponential accumulation of the PCR amplification product, this reaction is monitored in real time. From the output data of a so-called Real Time PCR, quantification a reliable back calculation to the input target DNA sequence is possible.

For the detection of minimal alterations on nucleic acid sequences found within alleles, genetic polymorphisms or the resulting transcripts the TaqMan™ technology can be adjusted. In this case, for every allele or polymorphism to be detected by TaqMan™ technology a specific oligonucleotide probe must be designed and used. These oligonucleotide probes differ in one or more nucleotides in accordance with the allele the probe shall bind to for TaqMan™ PCR assay. Additionally, for every allele the corresponding oligonucleotide probes comprise a different colored fluorescent reporter dye. Thus, by performing the TaqMan™ PCR assay every allele or polymorphism is recognized by the probe that specifically binds to its sequence. During PCR, the fluorogenic signal of the specific probe is released. Since the released fluorogenic signals are different for every allele, it can be determined how many different alleles are present. However, to determine the quantity of each different allele, this method is unreliable or even not applicable.

Assuming that alleles only differ in one base, the corresponding fluorogenic probes used for TaqMan™ PCR assay also differ in only one base. In this case the specificity of the quantification assay is due to an inhibition of hybridization. Accordingly, the fluorogenic probes are of minor specificity. Since a probe specific for one allele differs from another allele only in one base, this minor difference will not prevent binding of said probe to the other—unspecific—allele. Thus, it happens that in a TaqMan™ PCR assay the same fluorogenic signal will be released from different alleles. Accordingly, this fluorogenic signal cannot be used for a reliable quantification of the corresponding allele.

To summarize, technologies as known from the prior art are not suitable to quantify alleles or nucleic acid sequences with point mutations, small base pair deletions or insertions, especially, when said sequences represent less than 10% of the allelic sequences in the genome.

SUMMARY OF THE INVENTION

It is, thus, an object of the present invention to provide a highly sensitive and reliable assay capable to distinguish and especially to quantify nucleic acid sequences that differ in at least one base.

To achieve the foregoing and other objects, the present invention inter alia comprises the following, alone or in combination:

A method of quantifying alleles comprising nucleic acid sequences differing in at least one base wherein an allele-specific primer, forming a match with one allele but a mismatch with the other(s), is used for a real time PCR resulting in amplification of the allele that forms a match with the primer followed by quantification of said amplified allele as well as of the non-amplified allele;

the method as above, wherein said non-amplified allele forms a mismatch with the terminal 3' nucleotide of the allele-specific primer;

the method as above, wherein said allele-specific primer comprises additionally at least one mismatch;

the method as above, wherein said additional mismatch is at position −2 to −10 of the 3' tail of said allele-specific primer;

the method as any above, wherein said allele-specific primer forms a match with a minor allele present in smaller amounts than the non-amplified allele(s);

allele-specific primers with the sequence:
 AS5 (SEQ ID No.: 1);
 AS6 (SEQ ID No.: 2);
 AS7 (SEQ ID No.: 3);
 PIRA1 (SEQ ID No.: 5),
 AS1 (SEQ ID No.: 11),
 AS2 (SEQ ID No.: 12),
 AS3 (SEQ ID No.: 13), or
 AS4 (SEQ ID No.: 14);

allele-specific primers as above used for a method of quantification of alleles comprising mitochondrial DNA sequences differing in at least one base.

BRIEF DESCRIPTION OF THE DRAWINGS

The FIGURE is a schematic presentation of two alleles of the bovine mtDNA, which differ in one nucleotide in position 16057. The nucleotide positions of the mtDNA, hereinafter, refers to Anderson et al. (*J. Mol. Biol.* 156: 683–717 (1982)). The primer binding site of the forward (1) and reverse (2) primer are indicated. Stars mark the localization of sequence dependent mismatches between the primer and the template. Further indicated is the binding region of the oligonucleotide probe (5) with its attached fluorescent reporter dye (3) and quenching dye (4).

DETAILED DESCRIPTION OF THE INVENTION

Figure 1:
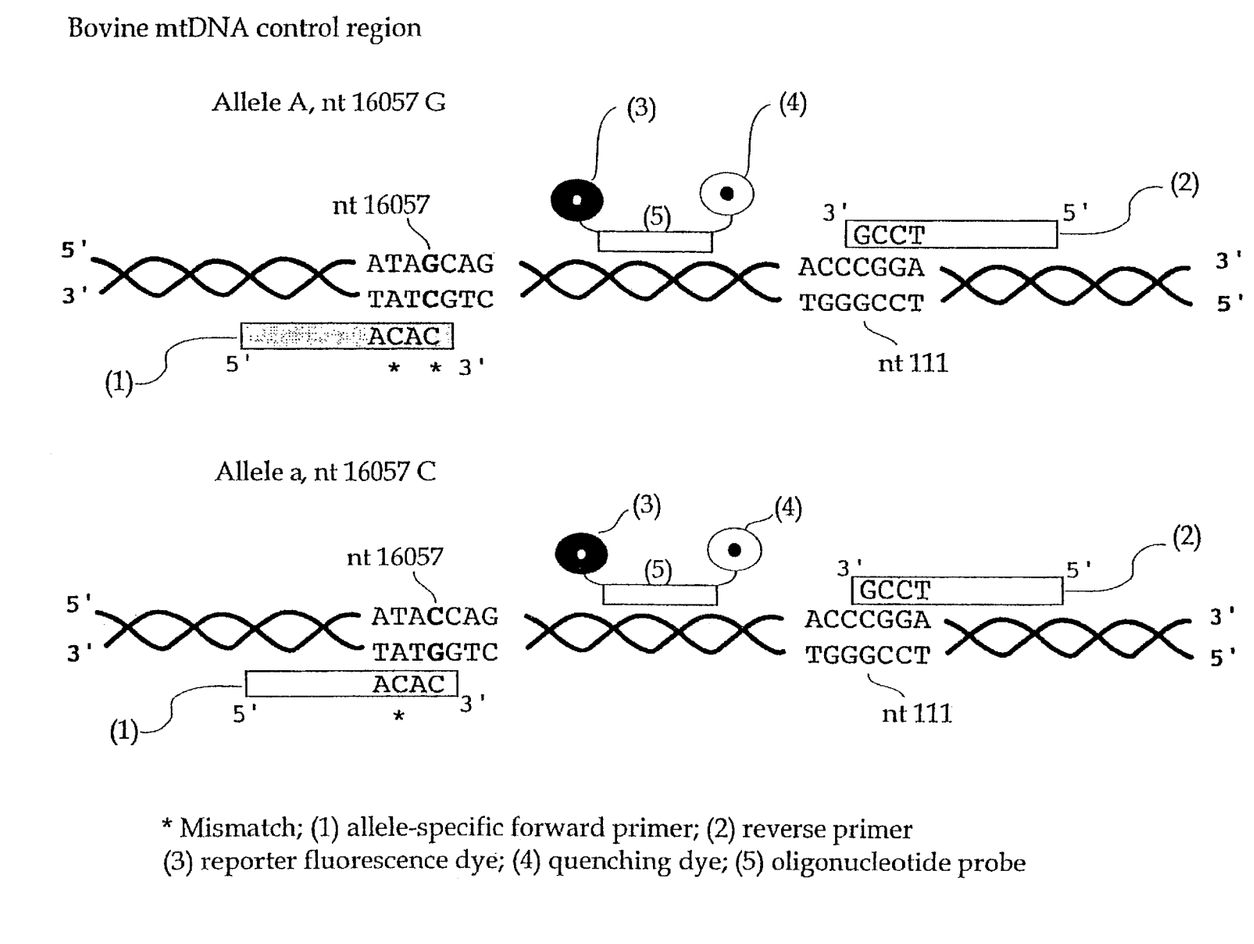

The present invention relates to a method of quantifying nucleic acid sequences differing in at least one base using Real Time PCR.

In its broadest aspect, the present invention provides a method of quantifying nucleic acid sequences differing in at least one base wherein an allele-specific primer, forming a match with one allele but a mismatch with the other(s), is used for a Real Time PCR. The primer-binding site of the allele-specific primer, according to the present invention, is selected in a way that the allele-specific primer binds at the location of the sequence variation of the allele to be quantified. Accordingly, said primer forms a match with the one allele but a mismatch with the other allele(s) at the location of the sequence variation. As a result of the match, said allele-specific primer forms with the one allele of the template nucleic acid sequences. This allele is amplified in a Real Time PCR assay. During the extension phase of the Real Time PCR assay, the 5'-Exonuclease activity of the Taq polymerase cleaves the fluorescent reporter dye (e.g. FAM, 6-carboxyfluorescein) from a hybridization probe and thereby releases fluorescent emission of the FAM at 518 nm, which can be determined.

The mismatch can be located at any position of the primer and is normally due to false base pairing between the nucleotides Adenine/Thymidin and/or Cytosine/Guanidine of the primer sequence with the allelic sequence. As a consequence of said mismatch, primer-binding stability is reduced. Due to said reduced binding stability of the allele-specific primer, this allele is not amplified in the Real Time PCR assay. As long as an allele is not amplified, no 5'-Exonuclease degradation of the labeled probe occurs. Consequently, the emission spectra of the reporter dye of the hybridization probe specific for this allele remains quenched by the second dye (e.g., TAMRA, 6-carboxytetramethylrhodamine) also attached to the hybridization probe. Therefore, no fluorescent signal of said non-amplified allele cannot be detected.

Nevertheless, also said non-amplified allele can be quantified. In the case that only two alleles are to be quantified, at first the fluorescent emission of the amplified allele is measured, as indicated above. Subsequently, a further Real Time PCR is performed using non allele-specific primers. Thus, fluorescent signals, which are released from both alleles, can be measured. Finally, the amount of the non-amplified allele is calculated by subtracting the determined emission value representing the amount of the amplified allele from the determined emission value representing the amount of both alleles. The main advantage of said amplification of both alleles is that an internal reference value is used.

Similarly, further alleles, i.e., more than two alleles, can be quantified. For this, the amount of the first allele as well as the amount of all alleles is determined in a Real Time PCR, as described above. Additionally, the amount of all further alleles, except one non-amplified allele which will be calculated, have to be separately determined in a Real Time PCR. For every allele to be measured, a different allele-specific primer is used. These primers form a match only with the allele they are specific for, but form mismatches with all the other alleles. Irrespective of the number of alleles present in a sample, in a Real Time PCR assay said primers allow only amplification and, respectively, determination of an emission value of the allele they are specific for. Finally, the amount of the non-amplified allele is calculated by subtracting the separately determined emission values representing the amount of the first and further amplified alleles from the determined emission value representing the amount of all alleles.

It has been found that the quantification assay is highly sensitive in comparison with prior art quantification techniques. It has been surprisingly found that an allele, which represents only 0.01% of the allelic sequences in a genome, can still become amplified and quantified, respectively. Thus, the method according to the present invention for the first time provides a quantification assay, which enables to quantify an allele that represents less than 5% of the allelic sequences in a genome.

A further advantage of the method according to the present invention is the provision of high sample throughput obtainable by automatization. Moreover, compared with the state of the art methods the method according to the invention avoids involvement of working steps difficult to standardize, such as electrophoresis for the analysis of PCR products. Furthermore, due to the use of allele-specific primers only a single labeled probe, instead of labeled probes for every allele, is needed. This results in tremendous cost reduction compared with costs arising from standard technology assays.

The term "allele" as used, therein after, is not limited to the understanding of the variants of a gene in a diploid DNA genome (Rompp Lexikon Biotechnologie, Georg Thieme Verlag Stuttgart—New York, 1992), but is used in a broader manner. The term "allele" additionally comprises other nucleotide acid sequences with point mutations, deletions and/or insertions of one or more base pairs, such as mitochondrial DNA (mtDNA), messenger RNA (mRNA), viral DNA or RNA genomes or DNA of microorganisms. Consequently, the method of the present invention is applicable for the quantification of nucleic acid sequences of other systems.

For example, it is possible to analyze quantitative differences in parental, heteroplasmatic or mutated variants of mtDNA using the method according to the present invention. The distribution of parental mtDNA is of special interest for pedigree analysis of domestic animals. Normally predominantly maternal mtDNA is present in descendants, except for descendants generated by in vitro fertilization or cloning techniques. For the analysis of the mtDNA composition in the cloned offspring of livestock species, a reliable quantification for mtDNA of the progenitors is essential.

Further, in the context of mitochondrial diseases, such as optic neuropathy (LHON) and others (for review see Johns, *Nature Medicine* 2:1065–1068(1996)) a reliable assay to determine quantitative differences of mutated mtDNA is desirable. When considering diseases due to mtDNA defects, it is essential to consider the phenomenon known as heteroplasmy. This describes the presence of both mutant and wild-type mtDNA in the same tissue, cell and possibly within the mitochondrion. Furthermore, the proportion of mutant to wild-type genome is seen to vary between tissues and also throughout life. Therefore, much interest has been focused on the hypothesis that accumulating damage to mtDNA is of importance in aging and common neurodegenerative diseases, e.g. Parkinson's disease and Alzheimer's disease (Egensperger et al., *Neuropathol-Appl-Neurobiol.* 23(4):315–321(1997)). The method according to the invention provides for the first time a possibility for the determination and quantification of organ- and age-related levels of mutated mtDNA. As a result of such a quantitative determination of the mutated mtDNA, therapeutic approaches to cure e.g., an organ-related mitochondrial disease, can be applied directly to the involved organ.

As a further example, it is also possible to quantify the different RNA transcripts of allelic genes. Said quantitative analysis is especially of interest in cases that the transcripts of the different alleles, because of a sequence variation on the one allele, have different functional properties. The term "different functional properties" comprises that an RNA transcript, including but not limited to mRNA, rRNA or tRNA, lost its capacity to induce or prevent a certain function. In this case an unbalanced or even predominant presence of said RNA transcript can correlate with a disease syndrome. One example for a disease caused by different functional properties of allelic transcripts is sickle cell-thalassemia disease which depends from the percentage of the mutated Hb (Roche Lexikon Medizin, Eds. Hoffman-LaRoche AG und Urban & Schwarzenberg, München, 1984). Reliable quantification of such RNA transcripts with different functional properties will influence decisions for further medical treatment. For quantification according to the method of the present invention, at first, said transcripts of allelic genes have to be reverse transcribed to cDNA. Subsequently, an allele-specific primer designed to form a match with the cDNA of a certain transcript is used in a Real Time PCR quantification assay to amplify and, respectively, quantify the amount of said certain transcript. As already described, the amount of both transcripts, independently their functional differences, is determined in a Real Time PCR using non allele-specific primers. Finally, the amount of the other non amplified transcript can be calculated as mentioned above.

The method according to the present invention is also applicable for the determination of differences between the wild-type genome of a virus and mutated genomes of subtypes thereof. For example, in case of Human Immunodeficiency Virus (HIV) it is known that resistance against a special drug is due to a specific mutation within the viral genome. According to the method of the present invention, the DNA, or respectively cDNA, of the mutated viral genome from a patient derived sample is amplified within a Real Time PCR using an allele-specific primer forming a match with said mutated genome but a mismatch with the wild-type genome, i.e., those viruses not comprising the specific mutation. After an additional Real Time PCR using non allele-specific primers to determine the amount of all viruses in the patient derived sample, the amount of the non-amplified, and thus, not mutated viral genomes can be calculated as described above. This quantification of the different viral subtypes in the virus population of a patient helps to decide on a drug therapy, which said virus population is still sensitive to.

Furthermore, the method of the present invention is applicable to quantify alterations in DNA of microorganisms, including extrachromosomal DNA of bacteria, cyanobacteria or fungi. Extrachromosomal DNA of microorganisms regularly comprises sequences encoding for proteins leading to a drug resistance or also toxic proteins. One example for a bacterium encoding a toxic protein on extrachromosomal DNA is *E. coli* subtype EHEC that can contaminate dairy products, raw meat or similar, and cause severe diarrhea or renal failure which leads quite often to death of the patient. Therefore, it is of special interest for the food industry to quantify the percentage of bacteria harboring DNA encoding for toxin genes. According to the method of the present invention, the amount of bacteria carrying extrachromosomal DNA encoding for toxin genes in a bacterial population can be quantified. For this, the extrachromosomal DNA encoding said toxin gene is amplified within a Real Time PCR using an allele-specific primer forming a match with said gene but a mismatch with corresponding sequences not encoding said gene. After a further Real Time PCR using non allele-specific primers to quantify the amount of extrachromosomal DNA present in the sample, the percentage of extrachromosomal DNA encoding for said toxin genes can be calculated as described above. Since the amount of extrachromosomal DNA per bacterium varies, a further Real Time PCR quantifying a single copy gene encoded on the extrachromosomal DNA is performed. In comparison with this further Real Time PCR quantifying a single copy gene encoded on the extrachromosomal DNA the percentage of bacteria encoding said toxin gene is determined. Similarly, the method according to the present invention can be applied to quantify the percentage of bacteria harboring extrachromosomal DNA encoding for a protein leading to a drug resistance. Especially for a proper treatment of a bacterial infection with antibiotics, it is important to know whether a patient's bacterial population is resistant to a certain drug. For this, the extrachromosomal DNA encoding said resistance gene is amplified within a Real Time PCR using an allele-specific primer forming a match with said gene but a mismatch with corresponding sequences not encoding said gene. In a second Real Time PCR, non allele-specific primers are used to quantify the amount of extrachromosomal DNA present in the sample. The percentage of bacteria encoding for said resistance gene can be calculated as described above. As a result of this quantitative analysis of the amount of bacteria resistant to a certain antibiotic treatment can be adjusted. Another example of microorganism encoding for a certain toxin gene is Pastorella, especially P. multocida. A Pastorella infection with a pathogenic strain of Pastorella e.g., in even-toed Ungulates, leads to haemoragies and within 3 to 4 days finally to death of the animal. Therefore, there is a high interest to recognize strain specific differences of Pastorella. According to the method of the present invention, a quantification of such strain specific differences is possible using an allele-specific primer specific to the pathogenic strain. As described before, the amount of the whole population of microorganisms is determined in a Real Time PCR using conventional primers. Additionally, the amount of a specific strain of Pastorella is quantified in a Real Time PCR using allele-specific primers.

In a preferred embodiment of the invention the primer is designed to form a mismatch at the terminal 3' nucleotide (the Figure) with the allele not to be amplified. This mismatch leads to an instability of the 3' end of the primer, resulting in a not fully hybridized 3' end. Consequently, this primer forming said mismatch is not elongated in a PCR and, respectively, the allele is not amplified in a Real Time PCR.

To further ensure that no amplification of the allele that form a mismatch with the primer occurs, at least one additional mismatch is introduced into the sequence of the allele-specific primer. The term "additional mismatch" comprises single and multiple base pair exchanges, insertions or deletions as well as chemical modifications of bases to the primer sequence. Such modifications disturb the natural occurring base pairing. Consequently, the introduction of such modifications e.g., introduction of a base analogue such as 3-nitropyrrole, a derivative of the nucleotide such as Xanthine/Hypoxanthine or derivative of the nucleoside such as Inosine, leads to an additional mismatch of the allele-specific primer with both alleles. The position of said additional mismatch can be located everywhere in the primer sequence. An additional mismatch leads to enhance primer instability. Due to this increased primer instability, no amplification of said allele takes place in the Real Time PCR assay according to the invention. However, said additional mismatch also weakens the binding between primer and the allele, which forms a match with said primer and which should be amplified. It has, nevertheless, been found that Real Time PCR amplification still occurs.

According to a further embodiment of the present invention, the additional mismatch is positioned between nucleotide −2 and −10 of the 3' end of the primer. Preferably, the additional mismatch is a single base pair mismatch at nucleotide −3 of the 3' end of the primer. Alternatively, primers with two or more mismatches between position −2 to −10 of the 3' end can be designed.

The allele-specific primer can form the mismatch(es) with the major allele of the population. Usually, the major allele is defined as the wild-type or naturally occurring allele, which normally is predominantly present in a sample compared to the whole population of alleles. The minor allele is defined as the allele less present in said sample, which e.g., comprises an alteration or mutation. In another further embodiment according to the invention, the allele-specific primer forms a match with said minor allele, which subsquently is amplified and determined.

The allele-specific primers (Table 1) AS5 (SEQ ID No.: 1), AS6 (SEQ ID No.: 2) AS7 (SEQ ID No.: 3), PARA1 (SEQ ID No.: 5), AS1 (SEQ ID No.: 11), AS2 (SEQ ID No.: 12), AS3 (SEQ ID No.: 13) or AS4 (SEQ ID No.: 14) are especially used according to the method of the present invention for quantification of alleles comprising mitochondrial DNA (mtDNA) sequences differing in at least one base. Additionally, for quantification of alleles of the mtDNA the labeled oligonucleotide probe TMP (SEQ ID No.: 4) is used. Conventional primers TM1 (SEQ ID No.: 9), TM2 (SEQ ID No.: 10), CO1 (SEQ ID No.: 6), CO2 (SEQ ID No.: 7) or CO3 (SEQ ID No.: 8) are especially used for the quantification of the whole amount of alleles, which resembles as a value of reference 100% of alleles present in a specific system.

The following figures and examples will further illustrate the present invention. It will be well understood by a person skilled in the art that the provided figures or examples in no way may be interpreted in a way that limits the applicability of the technology provided by the present invention to these examples.

EXAMPLE 1

Cytoplast-blastomere fusion and related embryo cloning techniques are used for the production of elite embryos in livestock species. Thus, the parental mitochondrial DNA (mtDNA) in early cloned embryos (n=26) and its transmission and segregation in born animals obtained by intraspecific cytoplast-blastomere fusion in *Bos taurus* was investigated.

During oogenesis the mtDNA copy number is reduced to nearly one per organelle. Mitochondrial DNA replication will repopulate each organelle sometime after the blastocyst stage and lead to relatively pure populations of each genotype that pre-existed in the original parental organelle. Cloning by cytoplast-blastomere fusion is based on the transfer of whole blastomeres, which donor the nucleus (donor blastomere =DB) from cleavage stage embryos to enucleated meiotic metaphase II oocytes (recipient cytoplast=RC). The cytoplast which includes cytoplasmic organelles like RER, Golgi, SER, tubules and other maternal factors being important for cell-cell communication and oocyte development is involved in the reprogramming of the introduced nucleus. The cytoplast's mtDNA type is assumed to be transmitted to the cloned offspring (Plante, *Theriogenology* 38: 897–904(1992)). However, in the cloning process there are two sources, i.e. cytoplast- and blastomere-, of parental mtDNA in the context of one nuclear genome, which is surrounded by two types of cytoplasm.

To investigate the transmission of the mtDNA allelic differences in the bovine mtDNA control region was quantified. At first, and to have a comparison both types of parental mtDNA in cloned embryos of early developmental stages was determined by Primer Introduced Restriction Analysis (PIRA). The A to G transition at nt16022 allowed the differentiation of parental mtDNA used (nucleotide positions refer to Anderson et al, 1982). The rare allele 16022A present in the DB-mtDNA created a potential restriction site for NspI which was used for primer introduced restriction analysis. The primer PIRA1 (SEQ ID No.:

5) possessing a mismatch at position 3 from the 3' end, generated a NspI site in the PCR product amplified with PIRA1 (SEQ ID No.: 5) and CO2 (SEQ ID No.: 7). PCR amplification was carried out in a buffer containing 60 mM Tris-HCl (pH 8.5), 15 mM $(NH_4)_2SO_4$, 0.2 mM dNTPs, 1 µM of each primer, 2 units Taq polymerase (Life Technologies, Austria) and 1 µl template DNA. PCR amplification was performed in a 50 µl reaction volume on a RoboCycler® (Stratagene, USA). The amplification of embryonic material was carried out under hot start conditions applying Hot-wax beads® (Invitrogen, The Netherlands) which contained $MgCl_2$ giving rise to final concentrations of 1.5 mM. Each experiment included a NTC (no template control). The amplification was carried out routinely according to the following scheme: first cycle: 5 min 95° C./1 min at annealing temperature ($T_a$) 41° C./3 min at 72° C.; 38 cycles: 20 sec 95° C., 40 sec at $T_a$/ and 60 sec 72° C. and last cycle: 20 sec 95° C., 40 sec at $T_a$/180 sec 72° C. As a control for the intactness of template DNA the whole control region (CR) of bovine mtDNA was amplified with primers CO1 (SEQ ID No.: 6) and CO3 (SEQ ID No.: 8), performing a hot-start PCR with $T_a$=48° C., 1.5 mM $MgCl_2$.

In the last two cycles 1 µCi of [α32]P-dCTP was added to label the PCR product. 15 µl of this reaction was cut with 2 U NspI (Life Technologies, Austria) for 3 h and run on a 10% non-denaturing polyacrylamide gel. The DB-mtDNA was taken as a control for a complete restriction digest. Gels were analyzed on a Biorad MG525 phospho-imager (Bio-Rad Laboratories, Austria).

It was shown that until the blastocyst stage the amount of mtDNA in the cloned embryos was constant. The perentage of the DB-mtDNA compared to the RC-mtDNA are 13%, 13% and 9% for the 1-cell stage, the morula and the blastocyst, respectively.

Subsequently the transmission of parental mtDNA in three pairs of cloned calves after birth was assayed by allele-specific quantification according to the present invention. Therefore, clones were generated from donor embryos with differing numbers of blastomeres: 24-cells, 52-cells, and 92-cells. Total DNA was isolated from blood as described by Kawasaki (1990). Allele-specific primers AS5 (SEQ ID No.: 1), AS6 (SEQ ID No.: 2) and AS7 (SEQ ID No.: 3) were designed instead of conventional oligonucleotides to exclude a possible amplification of a false "mitochondrial allele." Therefore, an additional mismatch at position 3 from the 3' end of each primer was introduced.

The probe TMP (SEQ ID No.: 4) for the allele-specific TaqMan™ quantification was designed to anneal between the forward and reverse primer (the Figure). It consists of an oligonucleotide with a 5'-reporter dye (FAM, 6-carboxyfluorescein) and a quencher dye (TAMRA, 6-carboxytetramethylrhodamine) attached via a linker arm that is typically located at the 3' end. The probe and the allele-specific primers were of HPLC-grade. A Hot Start PCR was not necessary under these conditions. TaqMan® PCR was performed at 4 mM $MgCl_2$ (5 min at 95° C., 40 cycles for 15 sec at 95° C. and 1 min at 70° C.). To test the reliability of TaqMan™ PCR in each experiment the amplification of each sample was repeated three times using the same master-mix.

A computer algorithm compares the amount of reporter dye emission with the quenching dye emission (Q) in each step and each cycle during the PCR amplification, generating a ΔRn (also called ΔRQ, ΔRQ=R/Q) value. This value reflects the amount of hybridization probe that has been degraded. The algorithm fits an exponential function to the mean ΔRn values of the last three data points of every PCR extension cycle, generating an amplification plot. A relative fluorescent emission threshold is set based on the baseline of the ΔRn during the first 10–15 cycles. The algorithm calculates the cycle at which each PCR amplification reaches a significant (i.e., usually 10 times the standard deviation of the baseline) threshold ($C_t$). Therefore, the threshold cycle ($C_T$), i.e. the first cycle in which a PCR product was detected, is therefore given as a mean value. It was demonstrated for conventional Real Time TaqMan™ PCR that the calculated $C_t$ value is proportional to the number of target copies present in the sample (Heid, et al., 1997). Thus, the $C_t$ value is a quantitative measurement of the copies of the target found in any sample and the real-time PCR method allows for a very large assay dynamic range (approaching $10^6$-fold starting target).

In addition to the NTC as mentioned above a second type of control the NAC (no amplification control) was included. Therefore, total cellular DNA of cattle, which lacked the mitochondrial allele under study, was used. If the desired type of mtDNA was not available a plasmid (pTAg vector, R&D Systems, Germany) bearing the appropriate allele was used.

The ratio of parental mtDNA types was analyzed by two sets (each set in triplicate) of TaqMan™ experiments, which were necessary to quantify the percentage of DB-mtDNA compared to the total population of mtDNA molecules: (i) the determination of the total amount of mtDNA (NAC) and (ii) the allele-specific TaqMan™ PCR of interest.

The calculation for allele-specific quantification can be further illustrated by the following equation:

$$\sum_{n=1}^{n} x_n = z$$

z, total number of molecules; n, number of different alleles, and $x_n$, number of molecules represented by each allele. Instead of total numbers of molecules the allelic distribution can be given in percent to the entirety of molecules (z=100%). The determination of parameters involved in this equation is described in the following for a two-allelic system. The value z can be determined in a conventional Real Time PCR. The allele-specific quantification determines one of the two alleles, which is usually the less frequent one.

To summarize it could be shown for conventional 'in vitro fertilized' (IVF) embryos and for cloned embryos that the content of mtDNA is constant during early embryogenesis until the blastocyst stage suggesting an absence of mtDNA replication. Therefore, the ratio of parental mtDNA was in accordance with the estimated quantitative participation of mtDNA from the fusion partners. Evidence has been obtained for a low-level transmission of blastomere mtDNA (DB-mtDNA) into the cloned offspring, thereby generating a heteroplasmic population of mtDNA. This has implications for cloning livestock animals. The amount of DB-mtDNA was 13% and 18% in two animals of a clone which derived from a 24-cell morula (donor of blastomeres) and 0.6% and 0.4% in two calves of clonal origin derived from a 92-cell morula (Table 2). These values are in accordance with the tendency expected for neutral mtDNA segregation that the less cell divisions that have occurred in the donor embryo, the higher the amount of DB-mtDNA. We also found a strong decrease of DB-mtDNA, which was about three magnitudes in the third clone derived from a 52-cell morula stage.

EXAMPLE 2

The applicability of the present invention for the quantification of alterations in microorganisms, which include chromosomal and especially extrachromosomal DNA, is demonstrated in the following for the case of extrachromosomal DNA. As model we have used E. coli transformed with different plasmids, p169A and p169G. These plasmids represent a DNA construct consisting of a cloning vector (pTAg vector, R&D Systems, Germany) and the whole bovine mtDNA control region (nucleotide 15747 to 383; Steinbom et al., *Biochim. Biophys. Acta*.(1998)). The plasmids varied in the way that, p169A contained the mtDNA allele 169A, which carries the nucleotide A at position 169, and p169G contained the other allele 169G, carrying the nucleotide G at position 169. Plasmid DNA was isolated from the bacteria culture according to a standard miniprepation method. Commonly, the plasmid DNA is isolated at a concentration of 250 ng/µl and was subsequently diluted $10^4$ fold. The applicability of the allele-specific Real Time PCR for the quantification of different alleles of extrachromosomal DNA was demonstrated in experiments mimicking the in vivo situation in which a population of molecules contains different ratios of both plasmids. For this the amplifications were performed on a 1:2 serial dilution of the plasmid (p169A) harboring the allele 169A in the background of plasmid p169G, harboring the allele 169G.

For a quantification of the plasmids coding for the different alleles the fluorescent probe TMP (SEQ ID No.: 4) and the allele-specific primer AS7 (SEQ ID No.: 3) and as reverse primer TM1 (SEQ ID No.: 9) were used. As a surprising effect it was shown that the method according to the present invention remains highly specific even using an allele-specific primer with a nucleotide A as a terminal 3' end. In a second Real Time PCR the two conventional oligonucleotides TM1 (SEQ ID No.: 9) and TM2 (SEQ ID No.: 10) as well as the fluorescent probe TMP (SEQ ID No.: 4) were used to quantify the whole amount of plasmid. The expected differences in the threshold values—a 1:8 dilution ($2^3$ dilution steps) is expected to show three times later its threshold—were obtained for each of these serial dilutions. Thus, it was demonstrated in experiments mimicking the in vivo situation of mtDNA heteroplasmy, i.e. the occurrence of at least two mtDNA alleles in the same sample/cell, that the allele-specific Real Time PCR is a reliable quantification assay.

Furthermore, several parameters influencing the efficiency of Real Time PCR amplification were investigated. Such parameters are e.g., magnesium and salt concentrations, reaction conditions (i.e. time and temperature), size and composition of the expected amplification product, primer sequences, and sample purity. Due to the mismatch(es) of the allele-specific primer near its 3' end these types of primers are especially sensitive to sample purity. In preliminary experiments it was suggested that the quality of the DNA preparation might be a limiting factor for some allele-specific primers due to the specific primer sequence. Therefore, the issue of sample purity in relation to a possible inhibitory effect was analyzed for $10^3$ and $10^4$ dilutions of the original plasmid isolation. As a result of this experiment it was shown that no inhibitory effect using the above mentioned allele-specific primers for the allele-specific amplification was observed.

TABLE 1

Allele-specific oligonucleotides

| Oligonucleotide | 5'—3' sequence | 5'14 3' position | SEQ ID No.: |
|---|---|---|---|
| AS1 | gta ctt gct tat atg cat ggT(c) gt | 16044—16022 | 11 |
| AS2 | taa tta tat gta tta tgt acG(a) gg | 16079—16057 | 12 |
| AS3 | cca gca taa tga taa C(g)ca | 152—169 | 13 |
| AS4 | gag cac cag cat aat gat aaA(g) cg | 147—169 | 14 |
| AS5 | acc att gac tgt aat gtc T(g)at | 189—169 | 1 |
| AS6 | gcc cca tgc ata taa gca G(a)gt | 16022—16042 | 2 |
| AS7 | gca agt aca tga cct cta C(t)ac | 16037—16057 | 3 |
| PIRA 1 | atg tat ata gta gtt taa att aC(t)a t | 15997—16021 | 5 |
| CO1 | cac cat caa ccc cca aag ct | 15747—15766 | 6 |
| CO2 | cct gaa gaa aga acc aga tg | 16284—16265 | 7 |
| CO3 | ttg ggt taa gct aca tca ac | 383—364 | 8 |
| TM1 | ctt aat tac cat gcc gcg tga | 16159—16179 | 9 |
| TM2 | cca gct aca ata gat gct ccg | 131—111 | 10 |
| TMP | ttg acg gcc ata gct gag tcc | 99—79 | 4 |

The position refers to the numbering in the reference sequence (Anderson et al., 1982). Nucleotides generating a mismatch in the template DNA are printed as capital letters. The corresponding nucleotide of the reference sequence is given in brackets.

TABLE 2

Different ratio of mtDNA in cloned cattle quantified by allele-specific Real Time PCR.

| clone | sample | amount of mtDNA* | allele-specific Real Time PCR | % of DB—mtDNA |
|---|---|---|---|---|
| C24 | DB–24–cell | 20.8 ± 0.2 | 24.0 ± 0.0 | 100% |
|  | C24–1 | 23.1 ± 0.2 | 29.2 ± 0.1 | 13% |
|  | C24–2 | 20.3 ± 0.1 | 25.9 ± 0.2 | 18% |
|  | NAC1† | 20.3 ± 0.1 | 30.2 ± 0.1 | 0.9% |
| C52 | DB–52–cell | 20.9 ± 0.3 | 20.6 ± 0.3 | 100% |
|  | C52–1 | 21.0 ± 0.1 | 34.8 ± 1.1 | 0.006% |
|  | C52–2 | 21.0 ± 0.1 | 38.5 ± 0.6 | 0.0004% |
|  | NAC2 | 21.7 ± 0.3 | 40.0 ± 0.0 | 0% |
|  | NAC3 | 21.0 ± 0.1 | 40.0 ± 0.0 | 0% |
| C92 | DB–92–cell | 22.7 ± 0.1 | 23.4 ± 0.1 | 100% |
|  | C92–1 | 16.8 ± 0.1 | 24.8 ± 0.2 | 0.6% |
|  | C92–2 | 18.2 ± 0.1 | 26.7 ± 0.2 | 0.4% |
|  | NAC4 | 23.0 ± 0.1 | 40.0 ± 0.0 | 0% |

The total amount of mtDNA was determined by conventional TaqMan™ PCR; †, sample NAC1 represents plasmid DNA; NAC2-NAC4 represents native bovine mtDNA. The numbers in column "amount of mtDNA" and "allele-specific Real-Time PCR" represent the threshold cycle, i.e. the threshold value for monitoring the reporter fluorescence.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of quantifying alleles comprising variants of mitochondrial nucleic acid sequences, each variant differing in at least one base, wherein a variant-specific primer, forming a match with one variant but a mismatch with the other variants and a probe are added to a real time PCR mixture, resulting in amplification of the one variant that forms a match with said variant-specific primer thereby producing an amplified variant, followed by quantification of said amplified variant by the detection of fluorescence released from the annealed probe during amplification, and wherein the variant-specific primer is selected from the group consisting of:

| | |
|---|---|
| AS5 | (SEQ ID NO:1); |
| AS6 | (SEQ ID NO:2); |
| AS7 | (SEQ ID NO:3); |
| PIRA1 | (SEQ ID NO:5); |
| AS1 | (SEQ ID NO:11); |
| AS2 | (SEQ ID NO:12); |
| AS3 | (SEQ ID NO:13); and |
| AS4 | (SEQ ID NO:14). |

2. The method according to claim 1, wherein a non-amplified variant forms a mismatch with a terminal 3' nucleotide of the variant-specific primer.

3. The method according to claim 1, wherein said variant specific primer comprises at least one additional mismatch.

4. The method according to claim 3, wherein said additional mismatch is at position –2 to –10 of a 3' tail of said variant-specific primer.

5. The method according to claim 1, wherein said variant-specific primer forms a match with a minor variant present in smaller amounts than a non-amplified variant(s).

6. The method of claim 1, wherein the probe comprises SEQ ID NO: 4.

7. A method of quantifying alleles comprising variants of mitochondrial nucleic acid sequences, each variant differing in at least one base, wherein a variant-specific primer, forming a match with one variant but a mismatch with the other variants and a probe are added to a real time PCR mixture, resulting in amplification of the one variant that forms a match with said variant-specific primer thereby producing an amplified variant, followed by quantification of said amplified variant by the detection of fluorescence released from the annealed probe during amplification, and wherein the variant-specific primer is AS5 (SEQ ID NO: 1).

8. The method according to claim 7, wherein a non-amplified variant forms a mismatch with a terminal 3' nucleotide of the variant-specific primer.

9. The method according to claim 7, wherein said variant specific primer comprises at least one additional mismatch.

10. The method according to claim 9, wherein said additional mismatch is at position –2 to –10 of a 3' tail of said variant-specific primer.

11. The method according to claim 7, wherein said variant-specific primer forms a match with a minor variant present in smaller amounts than a non-amplified variant(s).

12. The method of claim 7, wherein the probe comprises SEQ ID NO: 4.

13. A method of quantifying alleles comprising variant of mitochondrial nucleic acid sequences, each variant differing in at least one base, wherein a variant-specific primer, forming a match with one variant but a mismatch with the other variants and a probe are added to a real time PCR mixture, resulting in amplification of the one variant that forms a match with said variant-specific primer thereby producing an amplified variant, followed by quantification of said amplified variant by the detection of fluorescence released from the annealed probe during amplification, and wherein the variant-specific primer is AS6 (SEQ ID NO: 2).

14. The method according to claim 13, wherein a non-amplified variant forms a mismatch with a terminal 3' nucleotide of the variant-specific primer.

15. The method according to claim 13, wherein said variant specific primer comprises at least one additional mismatch.

16. The method according to claim 15, wherein said additional mismatch is at position –2 to –10 of a 3' tail of said variant-specific primer.

17. The method according to claim 13, wherein said variant-specific primer forms a match with a minor variant present in smaller amounts than a non-amplified variant(s).

18. The method of claim 13, wherein the probe comprises SEQ ID NO: 4.

19. A method of quantifying alleles comprising variants of mitochondrial nucleic acid sequences, each variant differing in at least one base, wherein a variant-specific primer, forming a match with one variant but a mismatch with the other variants and a probe are added to a real time PCR mixture, resulting in amplification of the one variant that forms a match with said variant-specific primer thereby producing an amplified variant, followed by quantification of said amplified variant by the detection of fluorescence released from the annealed probe during amplification, and wherein the variant-specific primer is AS7 (SEQ ID NO: 3).

20. The method according to claim 19, wherein a non-amplified variant forms a mismatch with a terminal 3' nucleotide of the variant-specific primer.

21. The method according to claim 19, wherein said variant specific primer comprises at least one additional mismatch.

22. The method according to claim 21, wherein said additional mismatch is at position −2 to −10 of a 3' tail of said variant-specific primer.

23. The method according to claim 19, wherein said variant-specific primer forms a match with a minor variant present in smaller amounts than a non-amplified variant(s).

24. The method of claim 19, wherein the probe comprises SEQ ID NO: 4.

25. A method of quantifying alleles comprising variants of mitochondrial nucleic acid sequences, each variant differing in at least one base, wherein a variant-specific primer, forming a match with one variant but a mismatch with the other variants and a probe are added to a real time PCR mixture, resulting in amplification of the one variant that forms a match with said variant-specific primer thereby producing an amplified variant, followed by quantification of said amplified variant by the detection of fluorescence released from the annealed probe during amplification, and wherein the variant-specific primer is PIRA1 (SEQ ID NO: 5).

26. The method according to claim 25, wherein a non-amplified variant forms a mismatch with a terminal 3' nucleotide of the variant-specific primer.

27. The method according to claim 25, wherein said variant specific primer comprises at least one additional mismatch.

28. The method according to claim 27, wherein said additional mismatch is at position −2 to −10 of a 3' tail of said variant-specific primer.

29. The method according to claim 25, wherein said variant-specific primer forms a match with a minor variant present in smaller amounts than a non-amplified variant(s).

30. The method of claim 25, wherein the probe comprises SEQ ID NO: 4.

31. A method of quantifying alleles comprising variants of mitochondrial nucleic acid sequences, each variant differing in at least one base, wherein a variant-specific primer, forming a match with one variant but a mismatch with the other variants and a probe are added to a real time PCR mixture, resulting in amplification of the one variant that forms a match with said variant-specific primer thereby producing an amplified variant, followed by quantification of said amplified variant by the detection of fluorescence released from the annealed probe during amplification, and wherein the variant-specific primer is AS1 (SEQ ID NO: 11).

32. The method according to claim 31, wherein a non-amplified variant forms a mismatch with a terminal 3' nucleotide of the variant-specific primer.

33. The method according to claim 31, wherein said variant specific primer comprises at least one additional mismatch.

34. The method according to claim 33, wherein said additional mismatch is at position −2 to −10 of a 3' tail of said variant-specific primer.

35. The method according to claim 31, wherein said variant-specific primer forms a match with a minor variant present in smaller amounts than a non-amplified variant(s).

36. The method of claim 31, wherein the probe comprises SEQ ID NO: 4.

37. A method of quantifying alleles comprising variants of mitochondrial nucleic acid sequences, each variant differing in at least one base, wherein a variant-specific primer, forming a match with one variant but a mismatch with the other variants and a probe are added to a real time PCR mixture, resulting in amplification of the one variant that forms a match with said variant-specific primer thereby producing an amplified variant, followed by quantification of said amplified variant by the detection of fluorescence released from the annealed probe during amplification, and wherein the variant-specific primer is AS2 (SEQ ID NO: 12).

38. The method according to claim 36, wherein a non-amplified variant forms a mismatch with a terminal 3' nucleotide of the variant-specific primer.

39. The method according to claim 36, wherein said variant specific primer comprises at least one additional mismatch.

40. The method according to claim 39, wherein said additional mismatch is at position −2 to −10 of a 3' tail of said variant-specific primer.

41. The method according to claim 37, wherein said variant-specific primer forms a match with a minor variant present in smaller amounts than a non-amplified variant(s).

42. The method of claim 37, wherein the probe comprises SEQ ID NO: 4.

43. A method of quantifying alleles comprising variants of mitochondrial nucleic acid sequences, each variant differing in at least one base, wherein a variant-specific primer, forming a match with one variant but a mismatch with the other variants and a probe are added to a real time PCR mixture, resulting in amplification of the one variant that forms a match with said variant-specific primer thereby producing an amplified variant, followed by quantification of said amplified variant by the detection of fluorescence released from the annealed probe during amplification, and wherein the variant-specific primer is AS3 (SEQ ID NO: 13).

44. The method according to claim 43, wherein a non-amplified variant forms a mismatch with a terminal 3' nucleotide of the variant-specific primer.

45. The method according to claim 43, wherein said variant specific primer comprises at least one additional mismatch.

46. The method according to claim 45, wherein said additional mismatch is at position −2 to −10 of a 3' tail of said variant-specific primer.

47. The method according to claim 43, wherein said variant-specific primer forms a match with a minor variant present in smaller amounts than a non-amplified variant(s).

48. The method of claim 43, wherein the probe comprises SEQ ID NO: 4.

49. A method of quantifying alleles comprising variants of mitochondrial nucleic acid sequences, each variant differing in at least one base, wherein a variant-specific primer, forming a match with one variant but a mismatch with the other variants and a probe are added to a real time PCR mixture, resulting in amplification of the one variant that forms a match with said variant-specific primer thereby producing an amplified variant, followed by quantification of said amplified variant by the detection of fluorescence released from the annealed probe during amplification, and wherein the variant-specific primer is AS4 (SEQ ID NO: 14).

50. The method according to claim 49, wherein a non-amplified variant forms a mismatch with a terminal 3' nucleotide of the variant-specific primer.

51. The method according to claim 49, wherein said variant specific primer comprises at least one additional mismatch.

52. The method according to claim 51, wherein said additional mismatch is at position −2 to −10 of a 3' tail of said variant-specific primer.

53. The method according to claim 49, wherein said variant-specific primer forms a match with a minor variant present in smaller amounts than a non-amplified variant(s).

54. The method of claim 49, wherein the probe comprises SEQ ID NO: 4.

* * * * *

UNITED STATES PATENT AND TRADEMARK OFFICE
CERTIFICATE OF CORRECTION

PATENT NO.    : 6,518,025 B1
DATED         : February 11, 2003
INVENTOR(S)   : Ralf Steinborn et al.

It is certified that error appears in the above-identified patent and that said Letters Patent is hereby corrected as shown below:

<u>Title page, Item [54] and Column 1, line 2,</u>
Replace "Amplication" with -- Amplification --.

<u>Column 18,</u>
Line 37, replace "variant" with -- variants --.

Signed and Sealed this

Third Day of February, 2004

JON W. DUDAS
*Acting Director of the United States Patent and Trademark Office*